(12) United States Patent
Gruben et al.

(10) Patent No.: US 11,375,944 B2
(45) Date of Patent: Jul. 5, 2022

(54) APPARATUS FOR ASSESSING HUMAN BALANCE CAPABILITY

(71) Applicant: Wisconsin Alumni Research Foundation, Madison, WI (US)

(72) Inventors: Kreg George Gruben, Stoughton, WI (US); Wendy Lee Boehm, Madison, WI (US); Kieran Marc Nichols, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 727 days.

(21) Appl. No.: 15/354,254

(22) Filed: Nov. 17, 2016

(65) Prior Publication Data
US 2018/0132777 A1    May 17, 2018

(51) Int. Cl.
*A61B 5/00* (2006.01)
*A61B 5/103* (2006.01)
*A61B 5/11* (2006.01)

(52) U.S. Cl.
CPC ............ *A61B 5/4023* (2013.01); *A61B 5/103* (2013.01); *A61B 5/1036* (2013.01); *A61B 5/1121* (2013.01); *A61B 5/6887* (2013.01); *A61B 5/7278* (2013.01); *A61B 2562/0247* (2013.01); *A63B 2220/16* (2013.01); *A63B 2220/52* (2013.01); *A63B 2220/58* (2013.01)

(58) Field of Classification Search
CPC ... A61B 5/1036; A61B 5/1038; A61B 5/4023; A61B 2562/0219; A63B 2220/00; A63B 2220/10; A63B 2220/12; A63B 2220/13; A63B 2220/16; A63B 2220/50; A63B 2220/51; A63B 2220/52; A63B 2220/53; A63B 2220/56; A63B 2220/58; A63B 2220/54; A63B 24/0062; A63B 2024/0065; A63B 2024/0068; A63B 2024/0071
See application file for complete search history.

(56) References Cited

U.S. PATENT DOCUMENTS 9,168,420 B1 * 10/2015 Berme ............... A63B 24/0062

OTHER PUBLICATIONS

Internet Archive, Bertec Corporation 2015.*
Kreg G. Gruben et al.; "Mechanical interaction of center of pressure and force direction in the upright human." Journal of biomechanics 45. No. 9 (2012): pp. 1661-1665. Madison, WI.
Kreg G. Gruben et al.; "Force direction pattern stabilizes sagittal plane mechanics of human walking." Human movement science 31, No. 3 (2012): pp. 649-659.; Madison, WI.
Kuangyou B. Cheng "Does knee motion contribute to feet-in-place balance recovery?." Journal of biomechanics 49, No. 9 (2016): pp. 1873-1880.: University of Michigan, Ann Arbor, MI.
Wendy L. Boehm et al.; "Post-Stroke Walking Behaviors Consistent with Altered Ground Reaction Force Direction Control Advise New Approaches to Research and Therapy." Translational stroke research 7, No. 1 (2015): pp. 3-11; New York.

* cited by examiner

*Primary Examiner* — David J. McCrosky
(74) *Attorney, Agent, or Firm* — Boyle Fredrickson, S.C.

(57) ABSTRACT

An apparatus with one or more force plates senses of center-of-pressure and force-angle in the sagittal plane for a standing individual to provide an indication of balance capability based on the deduced functional relationship between center-of-pressure and force-angle within a limited band of frequencies. In one embodiment this relationship may be expressed as an intersection point of the force vectors with respect to the individual's center-of-mass.

17 Claims, 4 Drawing Sheets

APPARATUS FOR ASSESSING HUMAN BALANCE CAPABILITY

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to medical and therapeutic apparatuses and in particular to an apparatus for assessing an individual's balancing capabilities.

The ability of humans to remain upright while standing and walking requires a coordination of many different muscles, a process collectively termed balance. Loss of balance can disrupt daily life and increase the risk of falls, injury, and death. An ability to accurately assess an individual's ability to balance could provide insight into other medical conditions and inform intervention to prevent falling.

While there are many ways of measuring an individual's ability to maintain balance, for example, using the Berg Balance Test, many such methods may require a trained individual to conduct a test or can be relatively imprecise revealing changes in balance only after there has been significant loss of balance. The complex interaction of multiple neurological and musculoskeletal systems necessary for balance makes establishing a simple quantitative measurement of balance difficult.

SUMMARY OF THE INVENTION

The present invention provides an apparatus that can assess an individual's balance capability through measurements of the individual in a standing posture on a stationary rigid force-sensing platform. The assessment quantifies a relationship between a center-of-pressure and angle of force exerted by the individual over a period of time as measured by the force plate. This measurement may be distilled to a single "intersection point" value that can be compared to the individual's center-of-mass to assess balance or displayed for the purpose of balance rehabilitation. That intersection point summarizes the final common output of the complex neural-muscular-skeletal system in a manner that is directly relatable to the success or failure of meeting the mechanical demands of the balancing task.

Specifically, in one embodiment, the invention provides an instrument for assessing balance in an individual having at least one platform sized to receive an individual's foot applying a force against the platform with natural ankle freedom. A set of sensors communicates with the platform to provide a set of measurements determining a center-of-pressure of the force on the platform in a measurement plane of the foot and corresponding angle of the force on the platform within the measurement plane of the foot, and an analysis circuit receives input from the sensors to determine a functional relationship between the center-of-pressure and angle of force of the set of measurements. This functional relationship is output to provide an assessment of individual balance based on the functional relationship.

It is thus a feature of at least one embodiment of the invention to provide a simple and rapid assessment of individual's balance capabilities without the need for expert intervention.

The functional relationship may be a slope in the change in center-of-pressure versus a change in angle of force association.

It is thus a feature of at least one embodiment of the invention to combine force-angle and center-of-pressure, readily obtained with the force plate, to produce a simple value qualifying complex neuro-muscular-skeletal interactions in the individual.

The analysis circuit may apply a bandpass filtering to the input from the sensors passing spectral energy from 1-5 Hz.

It is thus a feature of at least one embodiment of the invention to isolate narrowband frequency relationships between force-angle and center of contact such as to provide improved insight into the? complex control phenomenon of balance.

The output may provide a comparison between the functional relationship and a measurement of the body of the individual.

It is thus a feature of at least one embodiment of the invention to develop a series of common reference points (each associated with a specific frequency) applicable longitudinally among individuals (normalized to the body size of the individual) to assist in the development of normal and abnormal balance capability in a population.

The measurement of the body of the individual may be an estimate of the height of the center-of-mass of the individual.

It is thus a feature of at least one embodiment of the invention to provide a standard against which the balance output can be assessed related to what appears to be the mechanism of generating posture-restoring forces and torques in the relationship between center-of-pressure and force-angle.

The output may be a function of an intersection point derived from an intersection of force lines-of-action passing through the center-of-pressure at the force-angle for each of the series of measurements.

It is thus a feature of at least one embodiment of the invention to provide a simple representation of balance capability in the location of the intersection point of lines of force in the individual, and particularly with respect to the individual center-of-mass.

The intersection point height may be calculated as an average value of $IP_z$ according to the following formula:

$$IP_z = CP_x/(F_x/F_z)$$

where $CP_x$ is a horizontal displacement of the center-of-pressure on the platform for a given measurement, $F_x$ is a horizontal force on the platform for a given measurement and $F_z$ is a normal force on the platform for a given measurement.

It is thus a feature of at least one embodiment of the invention to provide a simple calculation for determining intersection point height from quantities readily determined with the force plate.

The instrument may include at least two independent platforms each positioned to receive a different of corresponding left and right foot of the individual and each providing an independent set of measures of a center-of-pressure of the force on the platform in the measurement plane of the foot and corresponding angle of the force on the platform within the measurement plane of the foot for each foot and providing separate outputs for each foot.

It is thus a feature of at least one embodiment of the invention to permit separate assessments of the left and right leg balance mechanisms, for example, useful for assessing neurological-deficit-induced balance problems.

The output may also indicate weight of individual.

It is thus a feature of at least one embodiment of the invention to provide a multipurpose instrument that can, for example, be used for routine assessment of balance in a doctor's office or the like as well as providing weight measures.

These particular objects and advantages may apply to only some embodiments falling within the claims and thus do not define the scope of the invention.

DETAILED DESCRIPTION OF THE PREFERRED EMBODIMENT

Figure 1:
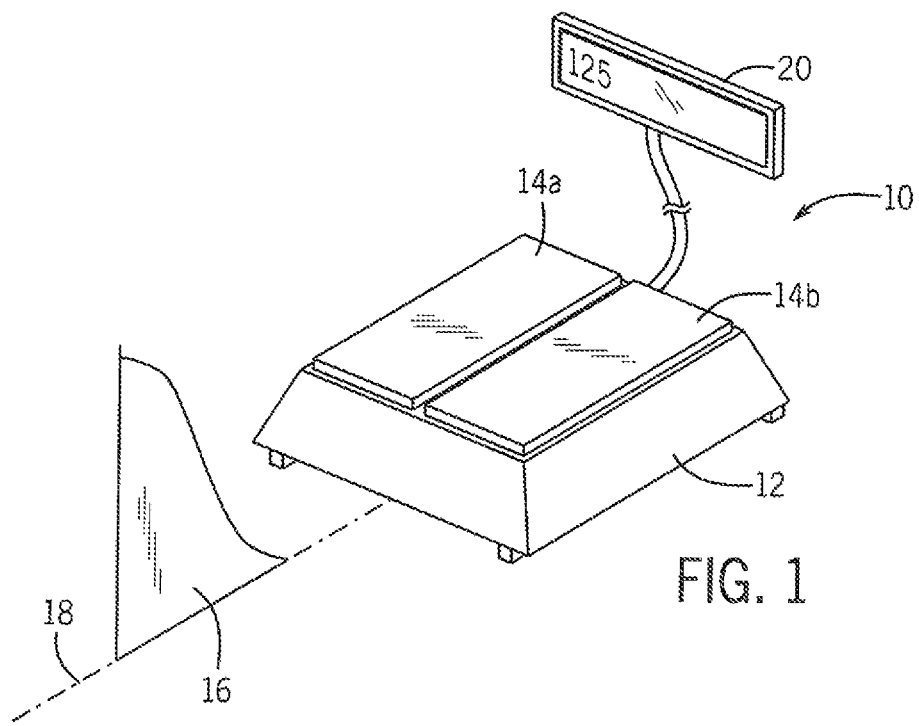
FIG. 1 is a perspective view of the present invention incorporated into a floor scale form factor having a remote readout to be visible to an individual standing on a scale platform.

Referring now to FIG. 1, in one embodiment, a balance assessment apparatus 10 may provide for a floor unit 12 having an upper exposed surface providing a first and second horizontally extending force plate 14a and 14b sized to receive a left and right foot of a standing individual. The floor unit 12 may be conveniently supported on the floor with the force plates 14a and 14b elevated slightly so that a user may step up onto the floor unit 12 without inconvenience. As so positioned on the floor unit 12, the individual's mid-sagittal plane 16 separates the force plates 14a and 14b extending along an anterior-posterior axis 18.

The floor unit 12 may be associated with an electronic display 20, for example, that may be mounted on a stand or wall to be viewed by the individual when the individual is standing on the floor unit 12. The electronic display 20 may provide for alphanumeric or graphic display as will be discussed below.

Generally, each of the force plates 14a and 14b are instrumented to independently measure a center-of-pressure exerted by the feet of the individual on the force plates 14a and 14b and the angle of force applied against those plates by the user's feet. In this regard, and referring to FIG. 2, each force plate 14 may be rectangular and sized to receive within those rectangular perimeters soles of the user's feet. The force plates 14 are ideally a light-weight but stiff material such as an aluminum plate.

The corners of the force plate are supported from beneath by upwardly oriented force-sensors 22a-d each measuring downward force exerted by the force plate 14 transmitted through the force-sensors 22 to lower support surface 24 within the floor unit 12 generally contacting in parallel to the floor. Each of the force-sensors 22 may be, for example, a load cell measuring force along a vertical load cell axis 26 and may be separated from the support surface 24 by a ball bearing and race assembly 28 providing free translative movement (horizontal) in response to any horizontal component of the force exerted on force-sensor 22 thereby ensuring that only a vertical component of any force is measured by the force-sensors 22. Force-sensors 22 suitable for use with the present invention are described generally, for example, in US patent application 2014/0013862 published Jan. 16, 2014, and hereby incorporated by reference in its entirety.

Force plate 14 may be constrained to move only along anterior-posterior axis 18 with respect to the support surface 24 by means of linear bearings 30 on the support surface 24 engaging with downwardly extending guide pins 34 from the bottom of the force plate 14. Ideally this constraint is close to frictionless.

An additional force-sensor 22e may be oriented horizontally along the anterior-posterior axis 18 to be supported by a support bracket attached to the support surface 24 on an exterior face (not shown) and on an interior face to abut a tab 32 extending downwardly from the lower surface of the force plate 14. In this way the force-sensor 22e may measure forces on the force plate 14 in the horizontal plane directed along the anterior-posterior axis 18. A spring 36 extending horizontally between an upwardly extending bracket on the support surface 24 and a similar downwardly extending tab 38 may provide bias of the force plate 14 against the force-sensor 22e to ensure contact therebetween. Each of the force-sensors 22 may communicate with an internal microcontroller 40 having a processor unit 42 and a memory 44 holding a stored program 46. The microcontroller 40 may also communicate with the display 20 to provide for the display of alphanumerical or graphic data as will be discussed.

Figure 2:
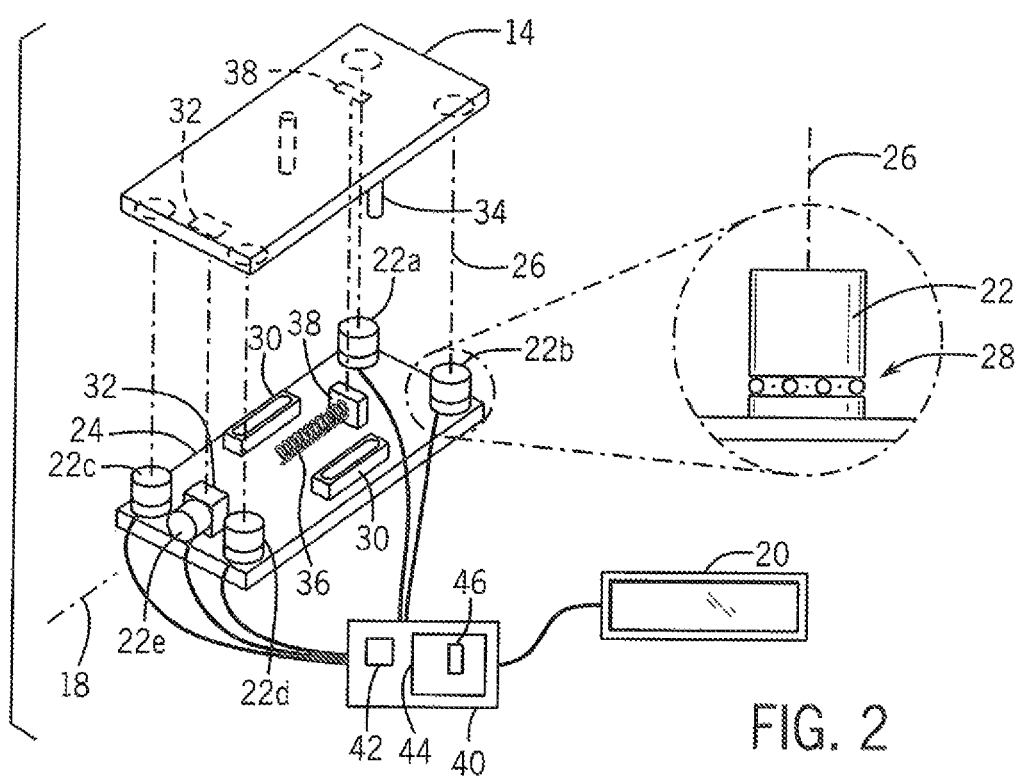
FIG. 2 is an exploded diagram of a force plate forming half of the platform of FIG. 1 such as may communicate with an electronic computer for making the balance measurements of the present invention.
Figure 3:
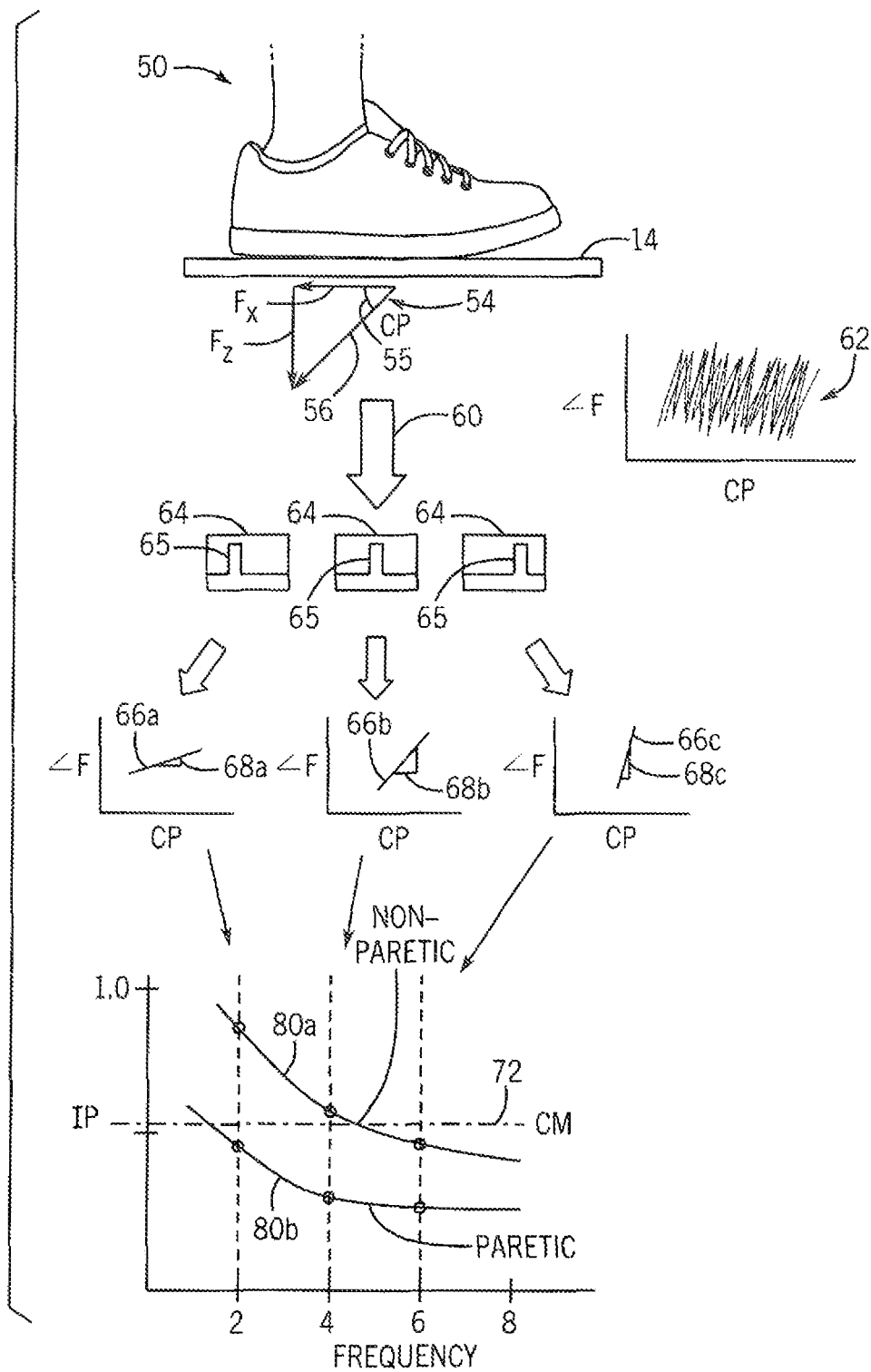
FIG. 3 is a data flow diagram showing the collection of a series of center-of-pressure and force-angle measurements, filtration, and analysis of the relationship between center-of-pressure and force-angle measurements underlying the series.
Figure 5:
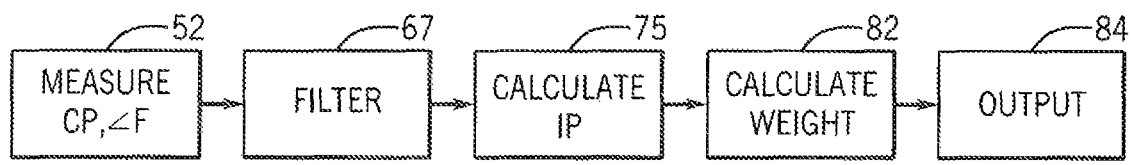
FIG. 5 is a flowchart depicting the processing of FIGS. 3 and 4 by an electronic computer of FIG. 2.

Referring now to FIGS. 2, 3 and 5, an individual 50 may stand on the force plates 14 for a predetermined period of time, as instructed, for example, by instructions received through the display 20. During these measurements, the individual's ankle, knee, and hip joints are generally unrestrained so as to permit the natural muscular forces required for balancing to be applied on these joints. During that period of time, as indicated by process block 52 a center-of-pressure 54 and force-angle 55 (in the sagittal plane of a foot aligned with each force plate 14a and 14b) may be collected at multiple points in time during the predetermined interval.

More specifically, the relative force on the force sensors 22a-22d may be used to determine the center-of-pressure 54. Because the center-of-pressure 54 is only required along a single dimension of the anterior-posterior axes, it will be appreciated that as few as two force sensors 22 may be used for this purpose. The sum of the forces from the sensors 22a-22d may also be used to deduce a downward force $F_z$ (being equal to the weight of the individual plus any accelerative forces). Similarly the force measured by force-sensor 22e may be used to deduce a horizontal force along the anterior-posterior axis 18 of $F_x$ (being equal to an accelerative force of balance exerted by the individual). These values, in turn, may be used to determine a force-angle 55, for example, determined as the arctangent of $F_x/F_z$.

The force-angle 55 and the center-of-pressure 54 find the location and direction of a ground reaction force vector 56 being a force vector which if applied to the force plate 14 (at the center-of-pressure 54 and having the force-angle 55) would produce the identical readings on each of the force-sensors 22 as provided by the distributed forces applied to the force plate by the individual's foot.

Force-sensors 22 produce a stream of data 60 representing different force vectors 56 at different sample points in time. If the relationship between center-of-pressure 54 and force-angle 55 is analyzed (for example, as shown in plot line 62), it portrays a complex relationship that is practically opaque to direct analysis. Accordingly, in the present invention, the stream of data 60 is filtered into multiple different frequency bins 64, for example, each having a one hertz passband 65 and arranged from 0 to 10 hertz (only three shown for clarity) as represented by process block 67. This filtration, for example, may make use of discrete frequency filters or may be performed using the fast Fourier transform generally known in the art.

Within each passband 65, the relationship between center-of-pressure 54 and force-angle 55 reveals a simpler relationship characterizable as different linear functions 66a-66c associated with a different passband 65, for example when discrete bandpass filters are implemented. Each of these linear functions 66 may have a different slope 68a-68, determined, for example, by the slope of a line fit to the data by linear regression or other similar technique.

Figure 4:
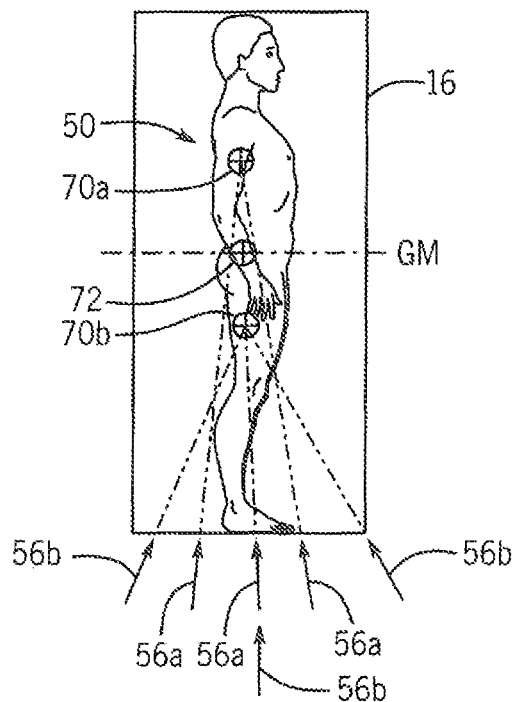
FIG. 4 is a simplified side elevational view of an individual bisected by a sagittal plane showing the analysis of center-of-pressure and force-angle in a series of measurements to define an intersection point above or below an individual's center-of-mass.

Generally the slopes 68 of this data for different frequency passbands 65 may be plotted as shown by graph lines 80a and 80b as will be discussed below. Preferably, however, the relationship between center-of-pressure 54 and force-angle 55 expressed by these linear slopes 68 are used to define an "intersection point" within the individual 50. Referring now also to FIG. 4, the intersection 70 is generally the point of intersection of each of the force vectors 56 associated with the stream of data 60. When the linear relationship between force-angle 55 and center-of-pressure 54 is associated with a relatively low slope 68 (e.g., shown by force vectors 56a), a high intersection point 70a will be identified resulting from the relatively low angular differences between the force vectors 56a for a given center-of-pressure displacement. Conversely when the linear relationship between force-angle 55 and center-of-pressure 54 is associated with a relatively high slope 68 (e.g., shown by force vectors 56b), a low intersection point 70b will be identified resulting from the relatively higher angular differences between the force vectors 56b for a given center-of-pressure displacement.

Generally this height may be calculated as $IP_z = CP_x/(F_x/F_z)$, per process block 75, where $IP_z$ is the height of the intersection point and $CP_x$ is lateral displacement of the center-of-pressure.

The height of the calculated intersection point 70 may be viewed with respect to a height of the individual's center-of-mass 72 to provide an intuitive understanding of the intersection point. In this regard, it is useful to analyze the height of the intersection point 70 with respect to the individual's center-of-mass 72. The center-of-mass 72 may be estimated based on the individual's height and similarities in human anatomy among individuals to be, for example, at a fixed percentage of the individual's height. Measurements producing force vectors 56a related to a relatively low slope 68 may identify an intersection point 70 being above the height of the center-of-mass 72. Conversely, measurements producing force vectors 56b related to a relatively high slope 68 may identify an intersection point 70b below the height of the center-of-mass 72.

Figure 6A:
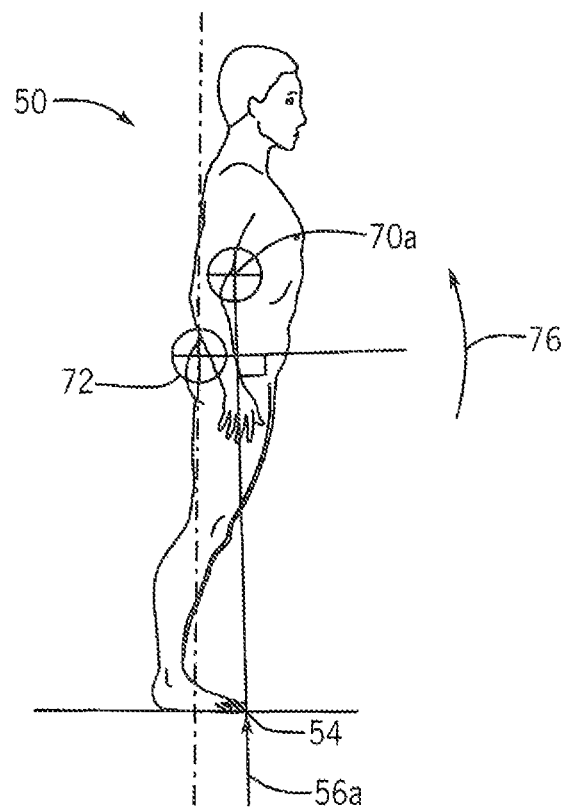
FIGS. 6a and 6b are figures similar to FIG. 4 showing an analysis of torque produced about an individual center-of-mass by the individual's balance response when the intersection point of that balance response is above or below the center-of-mass respectively.
Figure 6B:
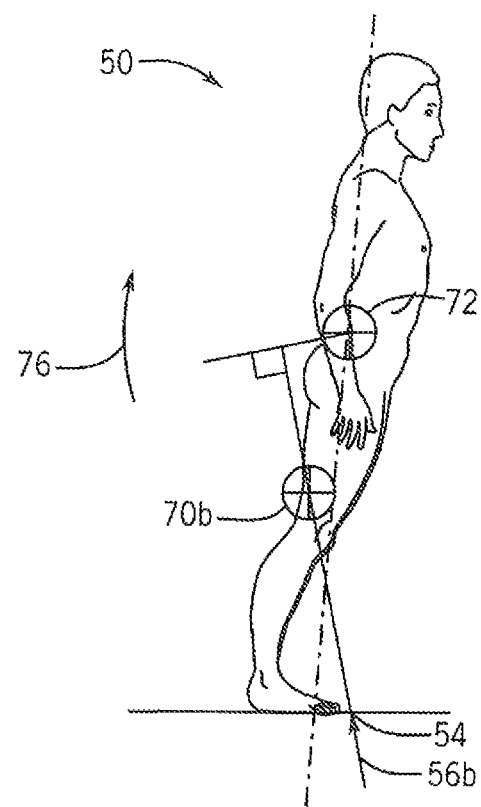

Referring now to FIGS. 6a and 6b, an insight into the significance of the intersection point 70 may be gained by considering the individual 50 as a rigid solid responding to torques applied by the individual's feet by rotating about the individual's center-of-mass 72. Referring to FIG. 6a, when the individual 50 is leaning forward (albeit stably with the center-of-mass 72 still behind the center of contact), and when the intersection point (70a) is above the center-of-mass 72, the torque about the center-of-mass 72 will be applied at an effective torque arm extending forward from the center-of-mass 72 and tending to restore the individual to upright posture with a counterclockwise torque 76. Conversely, however, and referring to FIG. 6b, in the same situation but where the intersection point 70b is below the center-of-mass 72, the torque will be applied to the center-of-mass 72 at a point on an effective torque arm extending rearward from the center-of-mass 72 causing a clockwise torque 76 tending to exacerbate the out-of-balance situation. Accordingly a control strategy producing a higher intersection point 70 may tend to be more stable.

Referring again to FIG. 3, this can be seen in a direct plot of the height of intersection points 70 as a percentage of normalized height of the individual for a non-paretic leg (indicated by plot line 80a) as compared to a paretic leg (affected by stroke and indicated by plot line 80b), for example, in frequencies centered around two hertz. The data for the non-paretic leg of plot line 80a in this frequency range shows an intersection point 70 well above the center-of-mass 72 while the plot line 80b of the paretic leg shows intersection point below the center-of-mass 72 generally indicating weaker balance in the paretic leg.

Referring again to FIG. 5, after calculation of the intersection point 70, the individual's weight may also be calculated, for example, by summing the values of the vertically oriented force-sensors 22 as indicated by process block 82. At process block 84 the balance information and weight information may be output on the display 20 either for assessment of balance capabilities or as part of a rehabilitation training system where the individual attempts to control this value with therapy. This therapy may involve the real-time observation of changes in the intersection point 70 as the individual concentrates on various aspects of his or her balance.

The output on the display 20 may be in various forms, for example, displaying any of the plots depicted in figures or displaying numeric values of slope or the like, or providing a graphic representation of the individual showing locations of intersection points and center-of-mass or providing a height measurement of the intersection point or a difference in height between the intersection point and the center-of-mass.

While the present invention has been discussed with respect to measuring force-angle and center-of-pressure for a standing individual, there is indication that the same measurements can be made with the individual in a seated position and instructed to press downward on a force plate 14, the latter tipped, for example, toward the individual to receive the individual's feet. In this case the intersection point is assessed as if the individual were standing and compared to the individual's standing center-of-mass. Again, the individual's ankle, knee joint, and hip joints are unrestrained except as related to their seated posture.

Although the above description describes measurements made in the sagittal plane of the individual, it is contemplated that other planes may equally provide comparable balance data and accordingly the invention contemplates measurements in other directions as well as along the sagittal plane axis.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. An instrument for assessing balance in an individual comprising:
   at least one platform size to receive an individual's foot applying a force against the platform with natural ankle freedom;
   a set of sensors communicating with the platform to provide a set of measurements determining a center-of-pressure of the force on the platform in a measurement plane of the foot and corresponding angle of the force on the platform within the measurement plane of the foot;
   an analysis circuit receiving a first set of multiple values of center-of-pressure as a function of time and a second set of corresponding multiple values of angle of force as a function of time from the sensors to determine at least one parameter of a predetermined function relating a change in angle of force to change in center-of-pressure over the multiple values;
   an output device providing an assessment of individual balance based on the parameter.

2. The instrument of claim 1 wherein the predetermined function is a slope of a change in the multiple values of center-of-pressure versus a change in corresponding multiple values of angle of force.

3. The instrument of claim 1 wherein the analysis circuit applies a bandpass filtering to the input from the sensors passing spectral energy primarily in a band between 1-5 Hz.

4. The instrument of claim 1 wherein the output provides a comparison between the predetermined function and a measurement of the body of the individual.

5. The instrument of claim 4 wherein the measurement of the body of the individual is an estimate of a height of a center-of-mass of the individual.

6. The instrument of claim 1 wherein the output is a function of an intersection point derived from an intersection of lines of action passing through a center-of-pressure at a force-angle for each of the set of measurements.

7. The instrument of claim 6 wherein the output is a function of intersection point height calculated as an average value of IPx according to a formula:

$$IPz = CPx/(Fx/Fz)$$

where CPx is a horizontal displacement of the center-of-pressure on the platform for a given measurement, Fx is a horizontal force on the platform for a given measurement and Fz is a normal force on the platform for a given measurement.

8. The instrument of claim 6 wherein the output provides an indication of a difference between a height of a center-of-mass of individual and the height of the intersection point.

9. The instrument of claim 6 wherein the output provides graphic representation of a height of the intersection point.

10. The instrument of claim 1 wherein the angle is determined by a measurement of a component of a force in the measurement plane parallel to a surface of the platform corrected by a force of the individual perpendicular to the surface of the platform.

11. The instrument of claim 1 including two independent platforms each positioned to receive a corresponding left and right foot of the individual and each providing an independent set of measures of a center-of-pressure of the force on the platform in the measurement plane of the foot and corresponding angle of the force on the platform within the measurement plane of the foot for each foot and providing separate outputs for each foot.

12. The instrument of claim 1 wherein the platform provides a rigid plate supported at four points by load cells measuring forces on the plate normal to the plate surface and restrained against sagittal motion by at least one load cell measuring forces on the plate parallel to the plate surface, signals from the five load cells determining a center-of-pressure of the force on the platform and a corresponding angle of force on the platform through combination.

13. The instrument of claim 1 wherein the output also provides a weight of the individual derived from a sum of signals from the load cells supporting the rigid plate at the four points.

14. The instrument of claim 1 wherein the measurement plane is parallel to the individual's sagittal plane as the individual is positioned on the platform.

15. A method of assessing balance in an individual using an instrument providing:

at least one platform size to receive an individual's foot applying a force against the platform with natural ankle freedom;

a set of sensors communicating with the platform to provide a set of measurements determining a center-of-pressure of the force on the platform in a measurement plane of the foot and corresponding angle of the force on the platform within the measurement plane of the foot;

an analysis circuit receiving a first set of multiple values of center-of-pressure as a function of time and a second set of corresponding multiple values of angle of force as a function of time from the sensors to determine at least one parameter of a predetermined function relating a change in angle of force to change in center-of-pressure over the multiple values;

an output device providing an assessment of individual balance based on the parameter; and the method comprising the steps of:

(a) placing an individual on the platform to obtain a set of measurements and to provide an output indicating an assessment of individual balance to the individual; and (b) instructing the individual to concentrate on changing the output in a particular direction;

(c) reading an output of the at least one parameter to diagnose balance problems in the individual.

16. The method of claim 15 wherein the output is a function of an intersection point derived from an intersection of lines of action passing through a center-of-pressure at a force-angle for each of the set of measurements.

17. The method of claim 15 wherein the measurement plane is parallel to the individual's sagittal plane as positioned on the platform.

* * * * *